US005192679A

United States Patent [19]
Dawson et al.
[11] Patent Number: 5,192,679
[45] Date of Patent: Mar. 9, 1993
[54] GROWING EHRLICHIA SPECIES IN A CONTINUOUS CELL LINE

[75] Inventors: Jacqueline E. Dawson, Atlanta, Ga.; Yasuko Rikihisa, Columbus, Ohio

[73] Assignee: The United States of America as represented by the Secretary of the Department of Health and Human Services, Washington, D.C.

[21] Appl. No.: 518,182

[22] Filed: May 3, 1990

[51] Int. Cl.[5] .......................... C12N 5/00; C12N 1/04

[52] U.S. Cl. ................................ 435/243; 435/240.1; 435/240.21; 435/260

[58] Field of Search .................... 424/88, 93; 435/235, 435/240.3, 240.21, 240.23, 253, 260, 258, 245

[56] References Cited

PUBLICATIONS

Stephenson "Canine Peritoneal Macrophages: Cultivation and Infection with *Ehrlichia canis*" Am J Vet Res. v 38, n 11, pp. 1815–1819 1977.

Wellman, A Macrophage-Monocfyte Cell Line from a Dog with Malignant Histiocytosis; In Vitro Cellular & Developmental Biology, vol. 24, No. 3, Part I, pp. 223–229, Mar., 1988.

Rikihisa, Yasuko, Growth of *Ehrlichia risticii* in Human Colonic Epithelial Cells; Annals New York Academy of Sciences, 590:104–110 (1990).

Hemelt, et al.,. Serial Propagation of *Ehrlichia canis* in Primary Canine Peripheral Blood Monocyte Cultures; Cornell Vet., 70:38–42 (1980).

Nyindo, et al., Tropical Canine Pancytopenia: In Vitro Cultivation of the Causative Agent-*Ehrlichia canis;* American Journal of Veterinary Research, vol. 32, pp. 1651–1658, 1971.

Dawson, et al., Serologic Diagnosis of Human Ehrlichiosis Using Two *Ehrlichia canis* Isolates; Journal of Infectious Diseases, vol. 163, pp. 564–567, 1991.

Holland, et al., Isolation, Experimental Transmission, and Characterization of Causative Agent of Potomac Horse Fever; Science, vol. 227, pp. 522–524, Feb., 1985.

Ristic, et al., Diagnosis of Equine Monocytic Ehrlichiosis (Potomac Horse Fever) by Indirect Immunofluorescence; JAVMA, vol. 189, No. 1, pp. 39–467, Jul., 1986.

Ristic, Miodrag, Pertinent Characteristics of Leukocytic Rickettsiae of Humans and Animals In Microbiology (ed.:Leive) American Society for Microbiology, pp. 182–187, 1986.

Holland, et al., Adaptation of *Ehrlichia sennetsu* to Canine Blood Monocytes: Preliminary Structural and Serological Studies with Cell Culture-Derived *Ehliichia sennetsu;* Infection and Immunity, pp. 366–371, May, 1985.

Cole, et al., Continuous Propagation of *Ehrlichia sennetsu* in Murine Macrophage Cell Cultures; Am. J. Trop. Med. Hyg., 34(4), pp. 774–780, 1985.

Stephenson,. et al., Somatic Cell Hybrids of Canine Peritoneal Macrophages and SV40-Transformed Human Cells: Derivation, Characterization, and Infection with *Ehrlichia canis;* Am. J. Vet. Res., vol. 41, No. 2, pp. 234–240, Feb., 1980.

Smith, et al., Isolation in Illinois of a Foreign Strain of *Ehrlichia canis,* The Causative Agent of Canine Ehrlichiosis (Tropical Canine Pancytopenia); JAVMA, vol. 166, No. 2, pp. 172–1745, 1975.

Brown, et al., In Vitro Cultivation of *Neorickettsia helminthoeca,* The Causative Agent of Salmon Poisoning Disease; Am. J. Vet. Res., vol. 33, No. 8, pp. 1695–1700, 1972.

*Primary Examiner*—Douglas W. Robinson
*Assistant Examiner*—Jane A. Williams
*Attorney, Agent, or Firm*—Cushman, Darby & Cushman

[57] ABSTRACT

The present invention relates to a method of continually propagating *Ehrlichia canis* in a microphage-monocyte cell line referred to as DH82.

5 Claims, 1 Drawing Sheet

GROWING EHRLICHIA SPECIES IN A CONTINUOUS CELL LINE

The present invention is related generally to the method of culturing microorganisms. More particularly, the present invention is related to a method of continually growing an obligate intracellular bacterium such as *Ehrlichia canis* (*E. canis*), *E. risticii*, *E. sennetsu*, *E. phagocytophila* and *Neorickettsia helminthoeca* in a canine macrophage cell line.

Human ehrlichiosis is a newly recognized rickettsial disease that has been reported from 19 states in the USA. The etiologic agent has not been isolated from a human, but seems to be serologically and morphologically related to *Ehrlichia canis*, a white blood cell associated rickettsia long recognized to cause both acute and chronic illness in dogs around the world.

Current research on human ehrlichiosis is dependent upon the in vitro growth of *E. canis*. *Ehrlichia canis* can be grown in primary canine monocytes, however, the life span of these cells is approximately 2-3 weeks, and a continual supply of blood from a dog is, therefore, necessary in order to maintain a very limited quantity of *E. canis* organisms.

A continuous mouse-dog hybrid (MDH) cell line has been developed for the purpose of in vitro cultivation of a Florida isolate of *E. canis*. No other cell line has heretofore been known or described for continual propagation of *E. canis*, either the Florida or the herein described Oklahoma isolate.

SUMMARY OF THE INVENTION

It is, therefore, an object of the present invention to provide a new method for continual propagation of *E. canis* in a cell line distinctly different from the MDH cell line.

Other objects and advantages will become evident from the following detailed description of the invention.

BRIEF DESCRIPTION OF THE DRAWINGS

The above and other objects, features and many of the attendant advantages of the invention will be better understood upon a reading of the following detailed description when considered in connection with the accompanying drawing wherein.

DETAILED DESCRIPTION OF THE INVENTION

Figure 1:
FIG. 1 represents a transmission electron micrograph of *E. canis*, Oklahoma isolate, in a membrane-bound vacuole in the cytoplasm of a DH82 cell. Note very pleomorphic structure of *E. canis* embedded in abundant capsular matrix. Ribosomes and fine DNA strands were visible. Bar=1 $\mu$m.

The invention comprises a demonstration of continual propagation of *E. canis* in a canine monocyte macrophage cell line DH82 in an in vitro medium that supports the growth of DH82 cells.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed or contemplated herein are standard methodologies well known to one of ordinary skill in the art. The materials, methods and examples are illustrative only and not limiting.

MATERIALS AND METHODS

The cultures of DH82 cell line employed in developing this invention, including those employed in the examples below, were obtained from the laboratory of Dr. Yasuko Rikihisa, Department of Veterinary Pathobiology, Ohio State University, Columbus, Ohio.

Isolation of *E. canis*

Primary canine monocyte cultures were established from a normal donor dog 48 hours before the arrival of the infected blood. Whole blood from the donor dog was transported in 2×15 cc heparinized tubes. After rinsing the tubes with 70% ethanol, the blood was transferred equally into 2 sterile erlenmeyer flasks and subsequently drawn into 2×60 cc syringes loaded with 20 ml of 2.5% dextran in saline. The needle was replaced and the syringe positioned needle-end up to allow for erythrocyte sedimentation. After 45 minutes, the leukocyte rich plasma from each syringe was transferred to 50 ml centrifuge tubes and spun at 50×g for 10 minutes. Each pellet was resuspended in 5 ml lysing buffer, held at room temperature (about 22°-24° C.) for 2 minutes and then centrifuged at 50×g for 10 minutes. The pellets were resuspended in 8 ml of culture medium (Minimum essential medium containing Earle's salts and sodium bicarbonate supplemented with 1% L-glutamine (200 mM) and 15% heat-inactivated homologous serum). Finally, the cell suspension was added equally to 4 25 cm$^2$ tissue culture flasks. The cultures were incubated at 37° C. for 24 hours at which time 5 ml of fresh culture medium was added. This procedure was repeated every 2 weeks in order to maintain a constant supply of primary canine macrophages.

Forty ml of whole blood drawn from a tick-infected carrier dog was sent to the Centers for Disease Control from Oklahoma State University. The infected blood was treated in a manner similar to the uninfected blood except that after the erythrocytes had sedimented, the leukocyte rich plasma was immediately transferred onto the 4 previously established primary canine monocyte cultures, and incubated at 37° C. for 24 hours. The leukocyte poor plasma was then decanted and 5 ml of culture medium was added to each flask and replaced every 3-4 days. Since primary canine macrophages only survive in vitro for a couple of weeks, the original cultures were harvested after two weeks and transferred to new primary canine macrophage cultures established 2-3 days earlier.

Starting 10 days after the addition of the leukocytes from the carrier dog, the cells were checked for infectivity. Briefly, 1 ml of supernatant from each culture was loaded into a cytospin (Shandon Inc., Pittsburgh, Pa.). The cells were centrifuged onto a glass slide, fixed in acetone for 15 minutes and then stained by direct immunofluorescence. This procedure was repeated twice weekly until organisms were observed.

Culture of Ehrlichiae

One 2 cc vial of frozen DH82 cells, established from the neoplastic progenitor cells of canine malignant histiocytosis (Wellman et al, 1988, *In Vitro Cellular and Developmental Biology* 24:223-229) was rapidly thawed in a 37° C. water bath and then transferred to a centrifuge tube containing 10 ml of culture medium. After 10 minutes of centrifugation at 400×g, the supernatant was removed and the pellet resuspended in 4 ml of culture medium. The cell suspension was then transferred into a 25 cm² tissue culture flask.

After 5 days of incubation at 37° C., the monolayer was split 1:2. Since a very limited amount of the bacteria was available, the supernatant from a 60-70% infected primary canine monocyte culture was added to the DH82 cells along with 2 ml of fresh medium. This process was repeated 10 days later and then again in 8 days with regular media changes every 3 to 4 days. Once the ehrlichia were established in the DH82 cell line, the 15% canine serum in the growth medium was changed to 15% FBS.

Preparation of antigen slides for IFA

Cells from *E. canis* (Oklahoma isolate) infected DH82 cultures (80-90% infection) were suspended in culture supernatant. Drops (10 μl) of the antigen suspension were placed onto 12 well teflon coated slides. The slides were air dried for 1 hour, wrapped in lint-free tissue and stored at −90° C. As slides were needed, they were thawed and then fixed in acetone for 15 minutes.

Serologic comparison of commercially prepared *E. canis* (Florida isolate) and DH82 (Oklahoma isolate) antigen slides A total of 15 human sera previously tested at CDC were used in a blind comparison study. Nine of the 15 patients were positive for antibodies to *E. canis* (Florida isolate). The 15 serum specimens were split into 2 sets, each coded with different numbers. The IFA (indirect fluorescent antibody) test was performed as described by (Fishbein et al, 1989, *J. Infect. Dis.* 160(5):803-809) on each serum set using the Oklahoma isolate in the DH82 cells and the commercially prepared slides with the Florida isolate in the MDH cells (*E. canis* antigen slides, Protatek, St. Paul, Minn.). Briefly, the serum sample was screened at a dilution of 64 in 0.15M PBS solution. When specific fluorescence was observed at this titer, serial two fold dilutions were made. Serologic results were reported as the reciprocal of the highest dilution at which specific fluorescence of *E. canis* morulae or individual bodies were observed.

Electron microscopy

Electron microscopy was performed as described by Rikihisa and Perry (1985, *Infect. Immun.* 49(3): 513-517). Briefly, infected macrophage cultures were fixed in a mixture of 2.5% paraformaldehyde, 5% glutaraldehyde, and 0.03% trinitrophenol in 0.1M cacodylate buffer (pH 7.4) and postfixed in 1% osmium tetroxide in 1.5% potassium ferrocyanide. After block staining in 1% uranyl acetate in maleate buffer (pH 5.2), cells were dehydrated in a graded series of ethanol and propylene oxide and embedded in Poly/Bed 812 (Polysciences, Inc., Warrington, Pa.). Thin sections (60 to 90 nm) were cut and stained with uranyl acetate and lead citrate and examined with a JEM 100 CXII electron microscope.

RESULTS

Cultivation of *E. canis*

*Ehrlichia canis* (Oklahoma isolate) morulae were first observed in the primary canine macrophage cells 30 days, and 3 blind passages, after the addition of the leukocyte rich plasma from the carrier dog. Similarly, morulae were observed in the continuous cell line 24 days after the first addition of infected supernatant. By day 29, 60% of the DH82 cells were infected and by day 37, 100% of the cells contained morulae. The supernatant was then used to infect normal DH82 cultures established 4 days previously. Also, infected cultures were split 1:4 and layered onto normal DH82 cells, or cultures that were 30-40% infected were split 1:2. All of these methods were determined to be equally effective in perpetuating the growth of *E. canis*.

Serologic comparison of commercially prepared and DH82 *E. canis* antigen slides The IFA results for 12 of the 15 sera were identical on both the commercial antigen slides prepared with the Florida isolate and the DH82 slides prepared with the Oklahoma isolate. Sera from one additional patient was twofold higher on the commercial slide. The remaining two sera were an acute and a convalescent sample from the same patient. The acute sample was seronegative on the DH82 slide and positive at a titer of 256 on the commercial slide. The results on the convalescent sample were positive on both slides. However, the convalescent result on the commercial slide was sixfold higher than on the DH82 slide (Table I).

Since all previous serologic tests for human ehrlichiosis were performed on the commercial slides with the Florida isolate, the sensitivity and specificity of the DH82 slides with the Oklahoma isolate were calculated based upon this standard. The specificity of the DH82 slides was determined to be 100%, while the sensitivity was about 87.5%.

In summary, the results presented herein clearly show that *E. canis* can be continually propagated in DH82 cell line in vitro in a suitable growth medium.

Other bacteria such as *E. risticil, E. sennetsu, E. phagocytophila*, and *Neorickettsia helminthoeca* are similarly propagatable in the DH82 cell line.

A deposit of *E. canis* infected and uninfected DH82 cell lines has been made at the ATCC. Rockville, Md. on Mar. 20, 1990 under the accession numbers CRL 10390 and CRL 10389, respectively. The deposit shall be viably maintained, replacing if it becomes non-viable during the life of the patent, for a period of 30 years from the date of the deposit, or for 5 years from the last date of request for a sample of the deposit, whichever is longer, and upon issuance of the patent made available to the public without restriction in accordance with the provisions of the law. The Commissioner of Patents and Trademarks, upon request, shall have access to the deposit.

It is understood that the examples and embodiments described herein are for illustrative purposes only and that various modifications or changes in light thereof will be suggested to persons skilled in the art and are to be included within the spirit and purview of this application and scope of the appended claims.

TABLE I

Indirect fluorescent antibody titers of 15 human sera tested with the Oklahoma and Florida *E. canis* isolates from DH82 and commercially prepared cells, respectively.

| Serum # | DH82/Oklahoma | Commercial/Florida |
|---|---|---|
| 1 | 64 | 128 |
| 2 | <64 | <64 |
| 3 | <64 | <64 |
| 4 | <64 | <64 |
| 5 | <64 | <64 |
| 6 | 512 | 4096 |

TABLE I-continued

Indirect fluorescent antibody titers of 15 human sera tested with the Oklahoma and Florida *E. canis* isolates from DH82 and commercially prepared cells, respectively.

| Serum # | DH82/Oklahoma | Commercial/Florida |
| --- | --- | --- |
| 7 | <64 | <64 |
| 8 | <64 | 256 |
| 9 | 512 | 512 |
| 10 | 256 | 256 |
| 11 | <64 | <64 |
| 12 | <64 | <64 |
| 13 | 256 | 256 |
| 14 | 8192 | 8192 |
| 15 | 2048 | 2048 |

What is claimed is:

1. A method for continually growing a bacterial pathogen comprising infecting the immortal, canine, macrophage cell line DH82 with *Ehrlichia canis* and cultivating the infected cells in a suitable culture medium until at least 30% of the DH82 cells are infected.

2. The method of claim 1 wherein at least 60% of the DH82 cells are infected.

3. A viable DH82 cell infected with *Ehrlichia canis*.

4. A culture of cells according to claim 3 in which at least 30% of said cells are infected.

5. A culture of cells according to claim 4 in which at least 60% of said cells are infected.

* * * * *

UNITED STATES PATENT AND TRADEMARK OFFICE
CERTIFICATE OF CORRECTION

PATENT NO. : 5,192,679
DATED : March 9, 1993
INVENTOR(S) : Jacqueline Dawson, et. al.

It is certified that error appears in the above-indentified patent and that said Letters Patent is hereby corrected as shown below:

On the Title page, item [57], line 2, delete "microphage" and insert -- macrophage--.

Column 4, line 36, delete "risticil" and insert --risticii--.

Signed and Sealed this

Thirtieth Day of November, 1993

Attest:

BRUCE LEHMAN

*Attesting Officer*  *Commissioner of Patents and Trademarks*